(12) United States Patent
Craine

(10) Patent No.: US 8,265,957 B2
(45) Date of Patent: Sep. 11, 2012

(54) METHODS, SYSTEMS, AND COMPUTER-READABLE MEDIA FOR DISEASE MANAGEMENT

(75) Inventor: Ari Craine, Marietta, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 1172 days.

(21) Appl. No.: 11/778,695

(22) Filed: Jul. 17, 2007

(65) Prior Publication Data

US 2008/0177570 A1    Jul. 24, 2008

Related U.S. Application Data

(60) Provisional application No. 60/881,081, filed on Jan. 18, 2007.

(51) Int. Cl.
G06Q 50/00 (2012.01)
G06Q 10/00 (2012.01)

(52) U.S. Cl. ................................. 705/3; 705/2
(58) Field of Classification Search .................... 705/2–3
See application file for complete search history.

(56) References Cited

U.S. PATENT DOCUMENTS

| | | | |
|---|---|---|---|
| 6,039,688 A * | 3/2000 | Douglas et al. | 600/300 |
| 6,494,830 B1 | 12/2002 | Wessel | 600/300 |
| 6,641,533 B2 | 11/2003 | Causey, III et al. | 600/300 |
| 6,931,328 B2 | 8/2005 | Braig et al. | 702/23 |
| 7,041,468 B2 | 5/2006 | Drucker et al. | 435/14 |
| 7,156,809 B2 | 1/2007 | Quy | 600/301 |
| 7,179,226 B2 | 2/2007 | Crothall et al. | 600/300 |
| 2007/0061393 A1 * | 3/2007 | Moore | 709/201 |

* cited by examiner

*Primary Examiner* — Sheetal R Rangrej
(74) *Attorney, Agent, or Firm* — Hope Baldauff Hartman, LLC

(57) ABSTRACT

Methods, systems, and computer-readable media provide for disease management. According to embodiments, a method for providing social interaction between a first handheld medical testing and monitoring device and a second handheld medical testing and monitoring device is provided. According to the method, at least one of a social networking profile and a diagnostic profile is received from the first handheld medical testing and monitoring device. A second user associated with the second handheld medical testing and monitoring device is selected based on the at least one of the social networking profile and the diagnostic profile. A user list at the first handheld medical testing and monitoring device is populated with a unique identifier enabling communication between a first user associated with the first handheld medical testing and monitoring device and the second user associated with the second handheld medical testing and monitoring device.

20 Claims, 8 Drawing Sheets

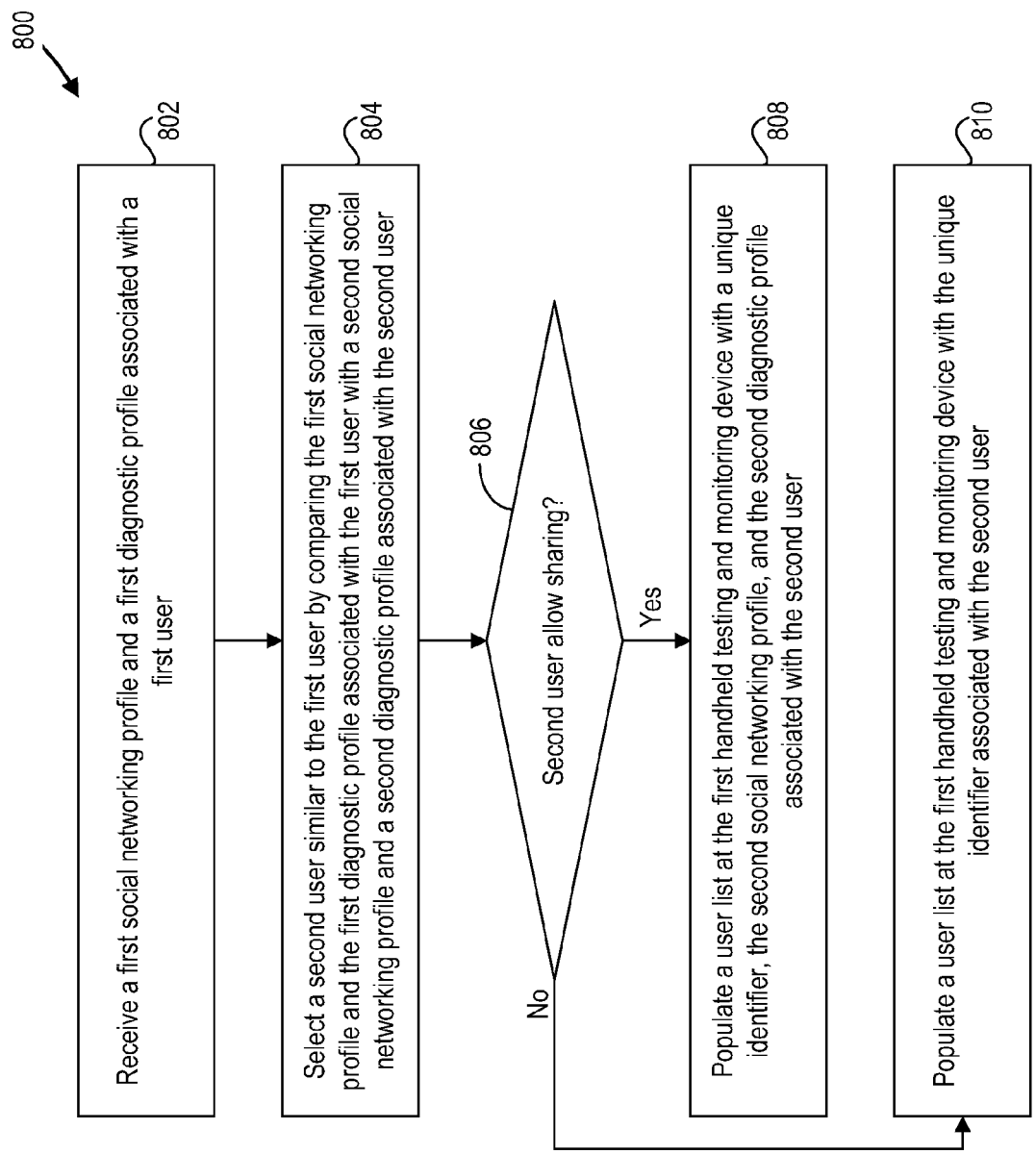

METHODS, SYSTEMS, AND COMPUTER-READABLE MEDIA FOR DISEASE MANAGEMENT

CROSS-REFERENCE TO RELATED APPLICATIONS

The present application claims priority to U.S. provisional patent application Ser. No. 60/881,081, filed on Jan. 18, 2007, which is hereby incorporated herein by reference.

TECHNICAL FIELD

This application relates generally to the field of medical devices. More specifically, the disclosure provided herein relates to the field of medical devices for disease management.

BACKGROUND

Active disease management generally requires a constant exchange of information between a patient, the patient's family, a caregiver, and a health-care professional (e.g., a physician). The health-care professional may seek regular diagnostic information regarding one or more conditions. The patient, the patient's family, and/or the caregiver may seek feedback associated with any changes in the diagnostic information. Acquiring regular diagnostic information, however, generally presents a significant challenge, especially for a health-care professional. For example, the patient may not be able to visit the health-care professional at adequate intervals due to time and/or cost constraints. A handheld medical testing and monitoring device may provide a cost-effective means with which to ensure constant communication between the patient and the health-care professional. An exemplary handheld medical testing and monitoring device is ONETOUCH, which is manufactured by JOHNSON AND JOHNSON.

The handheld medical testing and monitoring device may be configured to acquire diagnostic data related to a given condition at a given interval. For example, a diabetes-related monitoring device, such as ONETOUCH, may test the blood glucose level of a patient by collecting blood via a lancet prick and testing the collected blood. After the handheld medical testing and monitoring device acquires the blood glucose level of the patient, the handheld medical testing and monitoring device may transmit the blood glucose level over a network to a remote computer where the data is analyzed by, for example, the remote computer and/or a health-care professional. Based on patient's blood glucose level, the health-care professional may provide feedback, such as updated care information, to the patient, the patient's family, and/or the caregiver. Therefore, with the handheld medical testing and monitoring device, the health-care professional may remotely gather regular diagnostic information from the patient. With the regular diagnostic information, the health-care professional may timely provide the patient, the patient's family, and/or the caregiver potentially life-saving feedback in response to changes in the patient's diagnostic information.

SUMMARY

Embodiments of the disclosure presented herein include methods, systems, and computer-readable media for disease management. According to a first aspect, a method for providing social interaction between a first handheld medical testing and monitoring device and a second handheld medical testing and monitoring device is provided. According to the method, at least one of a social networking profile and a diagnostic profile is received from the first handheld medical testing and monitoring device. A second user associated with the second handheld medical testing and monitoring device is selected based on the at least one of the social networking profile and the diagnostic profile. A user list at the first handheld medical testing and monitoring device is populated with a unique identifier enabling communication between a first user associated with the first handheld medical testing and monitoring device and the second user associated with the second handheld medical testing and monitoring device.

According to a second aspect, a system for providing social interaction between a first handheld medical testing and monitoring device and a second handheld medical testing and monitoring device is provided. The system includes a memory and a processor functionally coupled to the memory. The memory stores a program containing code for providing social interaction between a first handheld medical testing and monitoring device and a second handheld medical testing and monitoring device. The processor is responsive to computer-executable instructions contained in the program and is operative to receive at least one of a social networking profile and a diagnostic profile from the first handheld medical testing and monitoring device, determine a second user associated with the second handheld medical testing and monitoring device based on the at least one of the social networking profile and the diagnostic profile, and populate a user list at the first handheld medical testing and monitoring device with a unique identifier enabling communication between a first user associated with the first handheld medical testing and monitoring device and the second user associated with the second handheld medical testing and monitoring device.

According to a third aspect, a computer-readable medium having instructions stored thereon for execution by a processor to perform a method for providing social interaction between a first handheld medical testing and monitoring device and a second handheld medical testing and monitoring device is provided. According to the method, at least one of a social networking profile and a diagnostic profile is received from the first handheld medical testing and monitoring device. A second user associated with the second handheld medical testing and monitoring device is determined based on the at least one of the social networking profile and the diagnostic profile. A user list at the first handheld medical testing and monitoring device is populated with a unique identifier enabling communication between a first user associated with the first handheld medical testing and monitoring device and the second user associated with the second handheld medical testing and monitoring device.

Other systems, methods, and/or computer program products according to embodiments will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

FIG. 8 is a flow diagram illustrating a method for providing social interaction between the first handheld glucose monitor and the second handheld glucose monitor, in accordance with exemplary embodiments.

DETAILED DESCRIPTION

The following detailed description is directed to methods, systems, and computer-readable media for disease management. In the following detailed description, references are made to the accompanying drawings that form a part hereof, and which are shown by way of illustration specific embodiments or examples.

For the sake of simplicity and without limitation, an invasive blood glucose monitor is illustrated in exemplary embodiments described herein. However, it will be appreciated by those of ordinary skill in the art that the described embodiments may be applicable for noninvasive blood glucose monitors, other suitable blood analyte monitors, and other suitable invasive and noninvasive medical testing and monitoring devices. Examples of other blood analyte monitors include, but are not limited to, monitors for testing cholesterol, triglycerides, and uric acid. Examples of other medical testing and monitoring devices include, but are not limited to, devices for testing and monitoring blood pressure, electrocardiogram ("ECG" or "EKG") activity, and heart rate.

Figure 1:
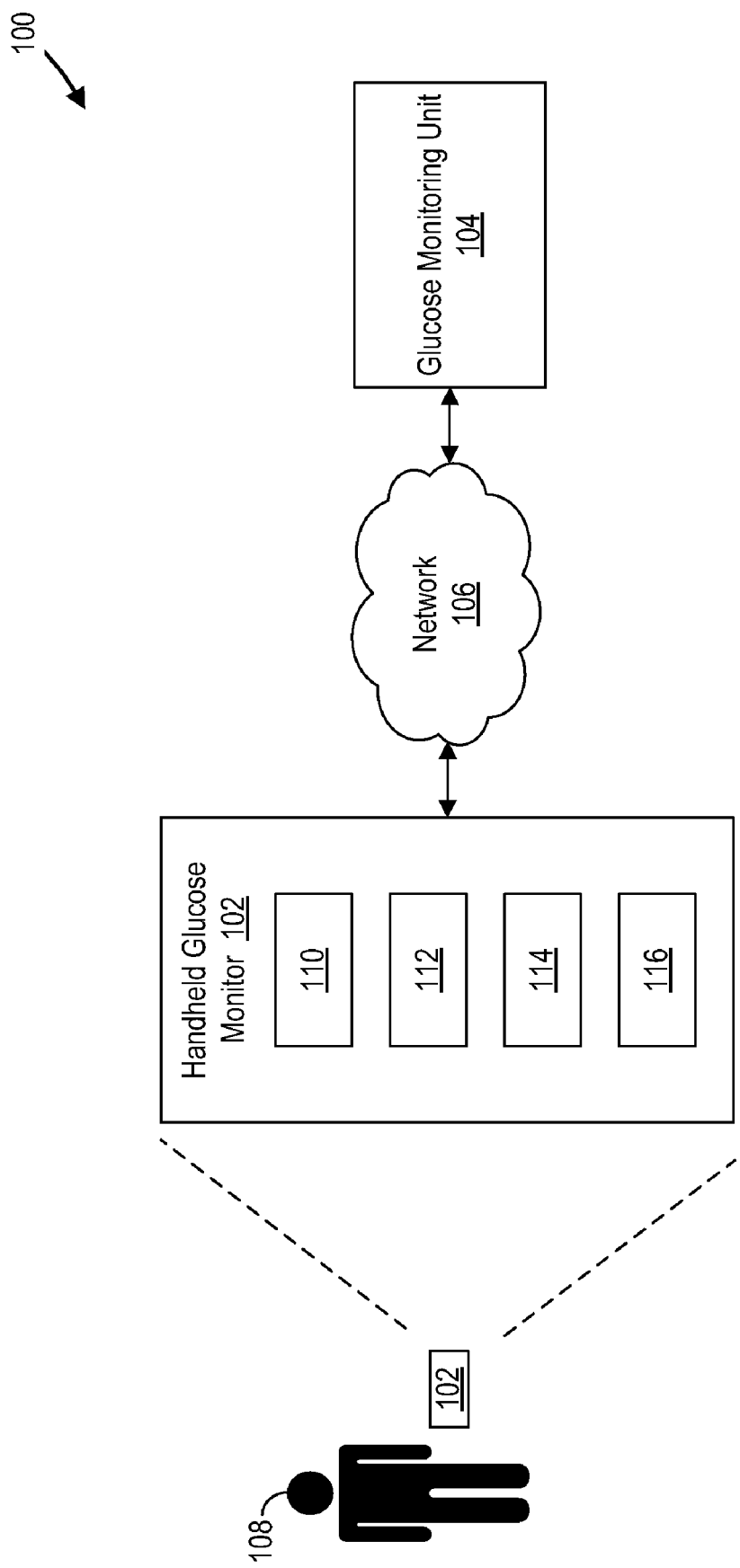
FIG. 1 is a block diagram illustrating a glucose monitoring system, in accordance with exemplary embodiments.

Referring now to the drawings, it is to be understood that like numerals represent like elements through the several figures, and that not all components and/or steps described and illustrated with reference to the figures are required for all embodiments. FIG. 1 is a block diagram illustrating a glucose monitoring system 100, in accordance with exemplary embodiments. The glucose monitoring system 100 includes a handheld glucose monitor 102, which is described in greater detail below. The handheld glucose monitor 102 is coupled to a glucose monitoring unit 104 via a network 106. According to exemplary embodiments, the handheld glucose monitor 102 is configured to collect a blood sample from a user 108 through, for example, a lancing device (not shown) on the handheld glucose monitor 102. After the blood sample is collected, the handheld glucose monitor 102 may process the collected blood sample to obtain a blood glucose level, which may then be transmitted to the glucose monitoring unit 104. According to exemplary embodiments, the glucose monitoring unit 104 is a computing device configured to receive blood glucose levels of the user 108 from the handheld glucose monitor 102 over the network 106. Communications between the handheld glucose monitor 102 and the glucose monitoring unit 104 may be encrypted to prevent an eavesdropper from accessing private medical information transmitted between the handheld glucose monitor 102 and the glucose monitoring unit 104.

As illustrated in FIG. 1, the handheld glucose monitor 102 includes a network adapter 110, an advertising module 112, a claims tracking module 114, and a social networking module 116. The network adapter 110 enables the handheld glucose monitor 102 to communicate with the glucose monitoring unit 104 over the network 106. Examples of the network adapter 110 may include, but are not limited to, a modem, a radio frequency ("RF") or infrared ("IR") transceiver, a telephonic interface, a bridge, a router, or a network card. The network 106 may include a wireless network such as, but not limited to, a Wireless Local Area Network ("WLAN") such as a WI-FI network, a Wireless Wide Area Network ("WWAN"), a Wireless Personal Area Network ("WPAN") such as BLUETOOTH, a Wireless Metropolitan Area Network ("WMAN") such a WiMAX network, or a cellular network. Alternatively, the network 106 may be a wired network such as, but not limited to, a Wide Area Network ("WAN") such as the Internet, a Local Area Network ("LAN") such as the Ethernet, a wired Personal Area Network ("PAN"), or a wired Metropolitan Area Network ("MAN"). It will be apparent to one of ordinary skill in the art that the glucose monitoring unit 104 may also include a network adapter, such as the network adapter 110.

Figure 3:
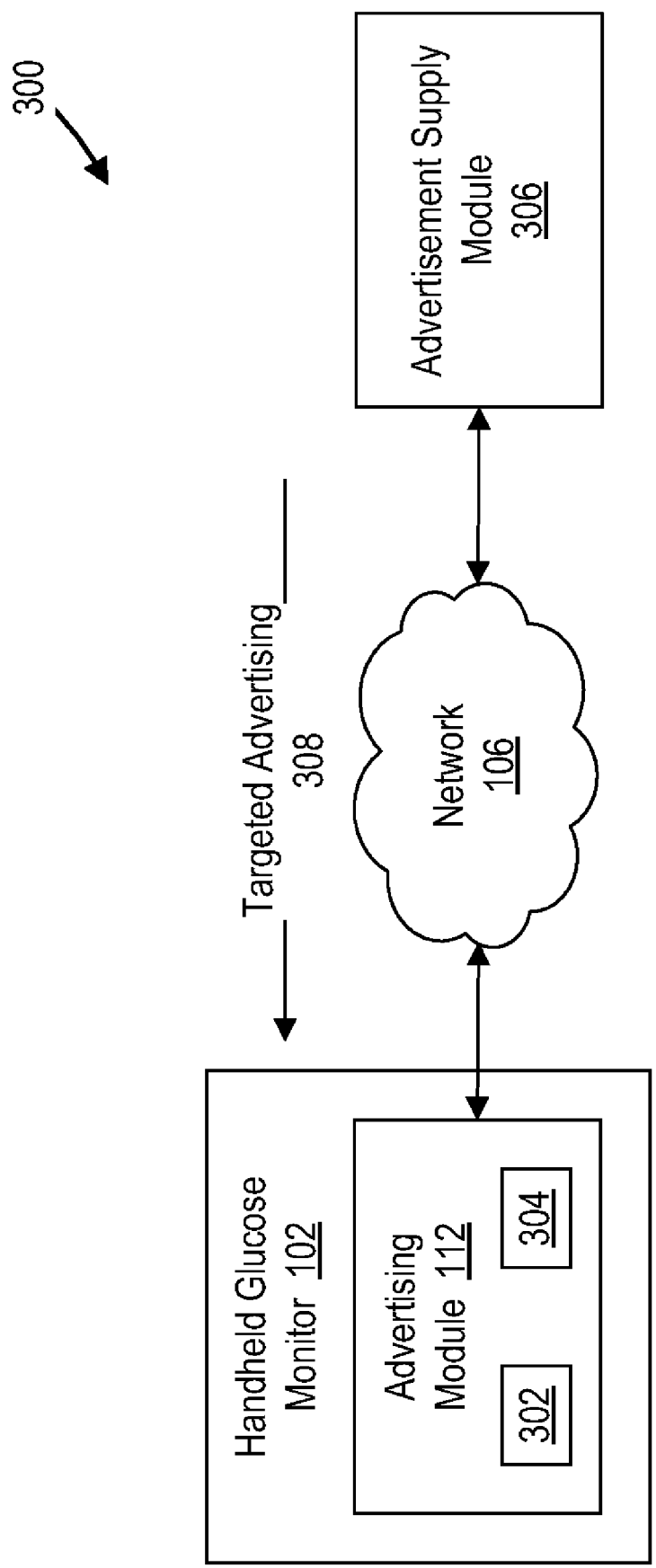
FIG. 3 is a block diagram illustrating an advertising system including the handheld glucose monitor 102, in accordance with exemplary embodiments.
Figure 4:
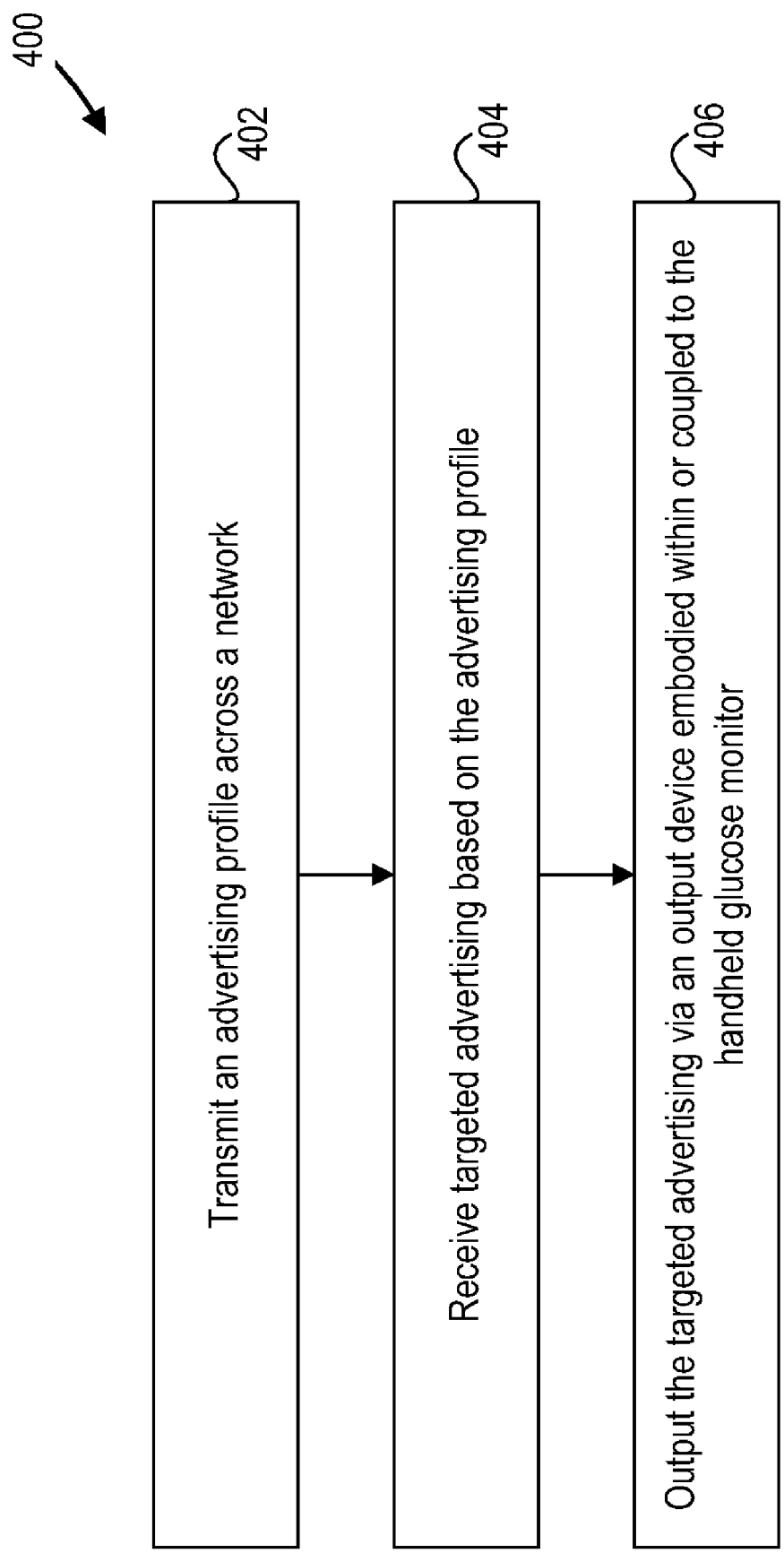
FIG. 4 is a flow diagram illustrating a method for receiving targeted advertising at a handheld glucose monitor, in accordance with exemplary embodiments.

According to exemplary embodiments, the advertising module 112, which is described in greater detail with respect to FIGS. 3 and 4, enables the handheld glucose monitor 102 to receive targeted advertising, such as targeted advertising 308. In one embodiment, the targeted advertising 308 is displayed via a display (not shown) on the handheld glucose monitor 102. The targeted advertising 308 may be targeted based on an advertising profile, such as an advertising profile 302, of the user 108. The advertising profile 302 may include any suitable criteria of the user 108 including, but not limited to, the user's age, location, and health condition. In one embodiment, the user's location may be determined using a positioning device (not shown), such as a global positioning system ("GPS") device, in the handheld glucose monitor 102. The targeted advertising 308 may provide a means by which the handheld glucose monitor 102 is subsidized, thereby making the handheld glucose monitor 102 more affordable for more users.

Figure 5:
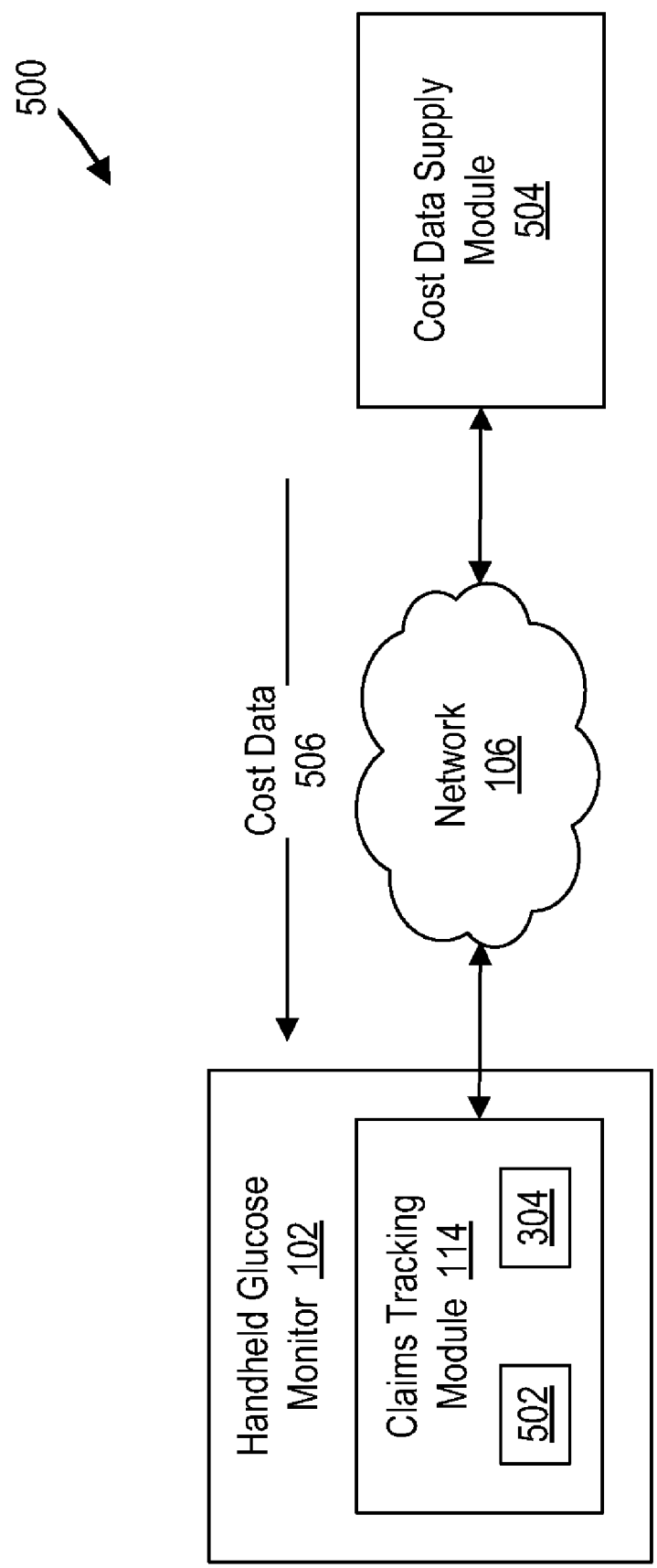
FIG. 5 is a block diagram illustrating a claims tracking system including the handheld glucose monitor 102, in accordance with exemplary embodiments.

According to exemplary embodiments, the claims tracking module 114, which is described in greater detail with respect to FIGS. 4 and 5, enables the user 108 to track cost savings and/or increases in response to the improving or declining health condition of the user 108. In one embodiment, after the handheld glucose monitor 102 determines the blood glucose level of the user 108, the claims tracking module 114 may determine that the health condition of the user 108 has improved over a given period of time. In response to the health condition of the user 108 improving, the claims tracking module 114 may display real and/or potential cost data, such as cost data 506, to the user 108 via the handheld glucose monitor 102. In one embodiment, the cost data 506 is displayed via a display (not shown) on the handheld glucose monitor 102. The cost data 506 may include, but is not limited to, decreases in visits with the health-care professional, decreases in drug usage related to regulating blood glucose levels, and decreases in overall insurance costs related to the improving health condition of the user 108. In further embodiments, the claims tracking module 114 may be aided by diagnostic data provided by the glucose monitoring unit 104 over the network 106. For example, the glucose monitoring unit 104 may track the blood glucose levels of the user 108 over a period of time to determine whether the health condition of the user 108 has improved.

According to exemplary embodiments, the social networking module 116, which is described in greater detail below with respect to FIGS. 7 and 8, enables the user 108 to find targeted "buddies" (also known as "peers," "contacts," "friends," and the like) from a social network of buddies including the user 108. Each buddy may be associated with a screen name or other unique identification ("ID"). A plurality of screen names may populate a buddy list with which the user 108 can use to communicate with buddies within the social network. In one embodiment, the social networking module 116 automatically finds at least one buddy based on a social networking profile, such as social networking profiles 702a and 702b, of the user 108. The social networking profiles 702a and 702b may include any suitable social criteria of the user 108 including, but not limited to, the user's age, location, and health condition. For example, the social networking module 116 may automatically find at least one buddy who is approximately the user's age, is within a given distance of the user's location, and shares at least one of the user's health conditions. In one embodiment, the user's location may be determined using a positioning device (not shown), such as a global positioning system ("GPS") device, in the handheld glucose monitor 102. The social networking module 116 may enable the exchange of medical information, such as information related to living with diabetes, and non-medical information, such information related to the newest blockbuster movie.

It should be appreciated by those of ordinary skill in the art that two or more of the advertising module 112, the claims tracking module 114, and the social networking module 116 may be utilized in conjunction to provide additional capabilities to the user 108, in accordance with exemplary embodiments. In one example, the same profile containing information related to the user 108, such as the user's age, location, and health condition, may be used by the advertising module 112 for providing targeted advertising and by the social networking module 116 for finding targeted buddies. In another example, targeted advertising provided by the advertising module 112 to the user 108 may be provided to other users on the buddy list of the user 108. In yet another example, cost savings data provided to the user 108 via the claims tracking module 114 may be shared with other users utilizing the social networking module 116. Other implementations utilizing two or more of the advertising module 112, the claims tracking module 114, and the social networking module 116 will become apparent to those of ordinary skill in the art in view of the present disclosure.

Figure 2:
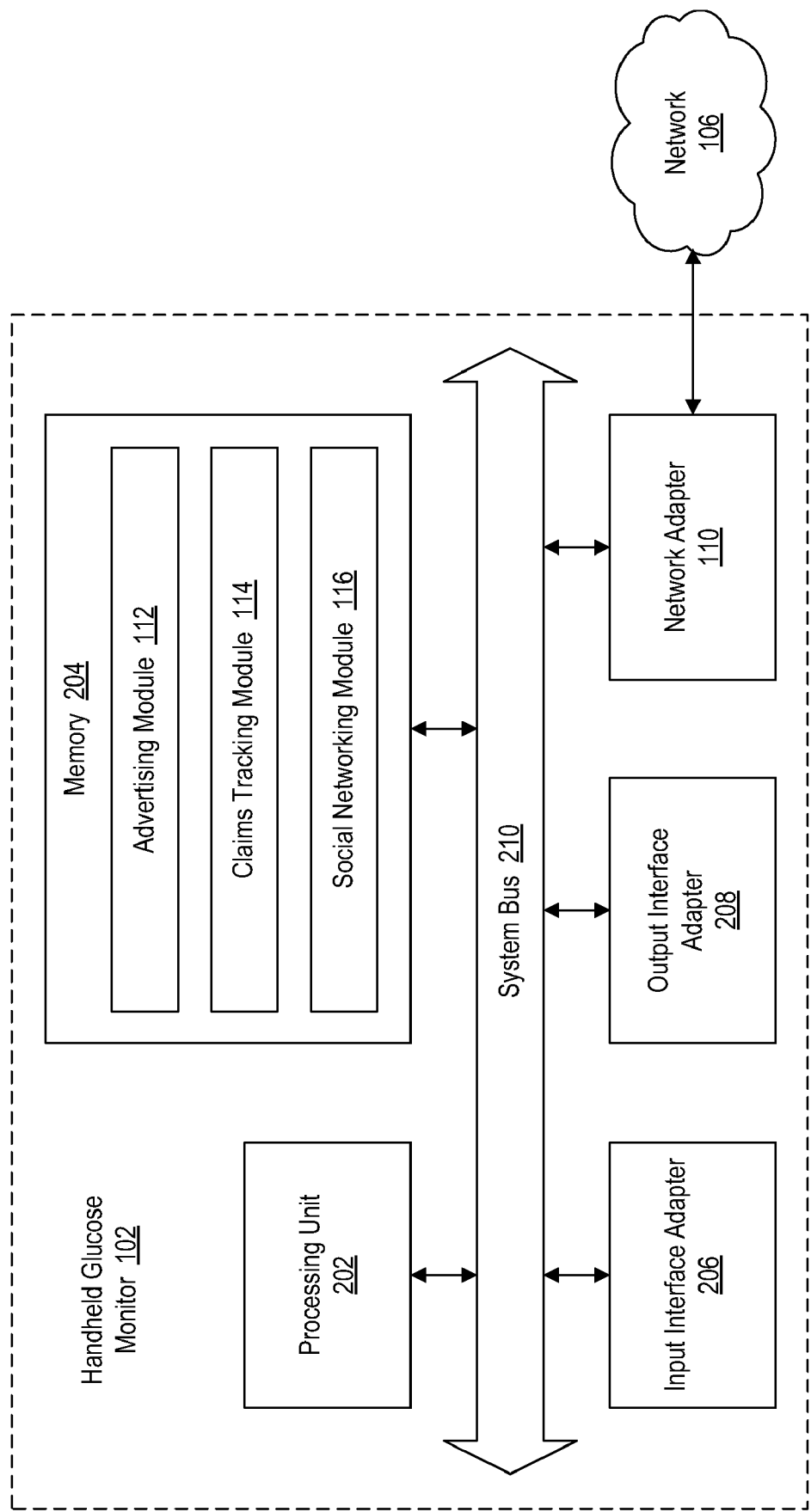
FIG. 2 is a block diagram illustrating a handheld glucose monitor, in accordance with exemplary embodiments.

FIG. 2 and the following discussion are intended to provide a brief, general description of a suitable computing environment in which embodiments of the handheld glucose monitor 102 may be implemented. While embodiments will be described in the general context of program modules that execute in conjunction with an application program that runs on an operating system on a computer system, those skilled in the art will recognize that the embodiments may also be implemented in combination with other program modules.

Generally, program modules include routines, programs, components, data structures, and other types of structures that perform particular tasks or implement particular abstract data types. Moreover, those skilled in the art will appreciate that embodiments may be practiced with other computer system configurations, including hand-held devices, multiprocessor systems, microprocessor-based or programmable consumer electronics, minicomputers, mainframe computers, and the like. The embodiments may also be practiced in distributed computing environments where tasks are performed by remote processing devices that are linked through a communications network. In a distributed computing environment, program modules may be located in both local and remote memory storage devices.

FIG. 2 is a block diagram illustrating the handheld glucose monitor 102, in accordance with exemplary embodiments. The handheld glucose monitor 102 includes a processing unit 202, a memory 204, an input interface adapter 206, an output interface adapter 208, and the network adapter 110, each of which is operatively connected to a system bus 210. The bus 210 enables bi-directional communication between the processing unit 202, the memory 204, the input interface adapter 206, the output interface adapter 208, and the network adapter 110. In further embodiments, the handheld glucose monitor 102 may be embodied within or coupled to any suitable portable computing devices including, but not limited to, laptop computers, personal digital assistants, cellular phones, and mobile media players configured to output audio, video, and other multimedia.

The processing unit 202 may be a standard central processor that performs arithmetic and logical operations, a more specific purpose programmable logic controller ("PLC"), a programmable gate array, or other type of processor known to those skilled in the art and suitable for controlling the operation of the server computer. Processing units are well-known in the art, and therefore not described in further detail herein.

The memory 204 communicates with the processing unit 202 via the system bus 210. In one embodiment, the memory 204 is operatively connected to a memory controller (not shown) that enables communication with the processing unit 202 via the system bus 210. The memory 204 includes the advertising module 112, the claims tracking module 114, and the social networking module 116 of FIG. 1. The advertising module 112 is described in greater detail below with respect to FIGS. 3 and 4. The claims tracking module 114 is described in greater detail below with respect to FIGS. 5 and 6. The social networking module 116 is described in greater detail below with respect to FIGS. 7 and 8. In exemplary embodiments, one or more of the advertising module 112, the claims tracking module 114, and the social networking module 116 are embodied in computer-readable media containing instructions that, when executed by the processing unit 202, perform a method as described in greater detail below with respect to FIGS. 4, 6, and 8, respectively. According to further embodiments, the advertising module 112, the claims tracking module 114, and the social networking module 116 may be embodied in hardware, software, firmware, or any combination thereof.

By way of example, and not limitation, computer-readable media may comprise computer storage media and communication media. Computer storage media includes volatile and non-volatile, removable and non-removable media implemented in any method or technology for storage of information such as computer-readable instructions, data structures, program modules, or other data. Computer storage media includes, but is not limited to, RAM, ROM, Erasable Programmable ROM ("EPROM"), Electrically Erasable Programmable ROM ("EEPROM"), flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the handheld glucose monitor 102.

The input interface adapter 206 receives data input from the user 108. The data may be input via any suitable input device, such as a keyboard or a stylus. The input devise may also be a medical testing device, such as a lancing device for collecting blood. The output interface adapter 208 outputs data to the user 108. The data may be output via any suitable output device, such as a display and a speaker. The input and output devices may be embodied within a single unit, such as a touch-screen display. The input and output devices may be embodied within or coupled to the handheld glucose monitor 102.

FIG. 3 is a block diagram illustrating an exemplary embodiment of an advertising system 300 including the handheld glucose monitor 102. As illustrated in FIG. 3, the handheld glucose monitor 102 includes the advertising module 112 described in FIGS. 1 and 2. The advertising module 112 includes the advertising profile 302 and a diagnostic profile 304 of the user 108. The advertising system 300 includes an advertising supply module 306. The handheld glucose monitor 102 is coupled to the advertising supply module 306 via the network 106. In one embodiment, the advertising supply module 306 is embodied within the glucose monitoring unit 104. In further embodiments, the advertising supply module 306 is separate from the glucose monitoring unit 104.

The advertising profile 302 may include any suitable advertising-related information about the user 108, such as the user's age, location, and health condition. The diagnostic profile 304 includes any suitable diagnostic data, such as the user's current and archived blood glucose levels, collected from the user 108 by the handheld glucose monitor 102, according to one embodiment. The archived blood glucose levels may include blood glucose levels collected within any suitable time frames.

In one embodiment, the advertising module 112 transmits the advertising profile 302 and the diagnostic profile 304 to the advertising supply module 306 over the network 106. In response to receiving the advertising profile 302 and the diagnostic profile 304, the advertising supply module 306 determines which advertisements to transmit to the user 108 based on the advertising profile 302 and the diagnostic profile 304. These selected advertisements are referred to herein as the targeted advertising 308. According to exemplary embodiments, the advertising supply module 306 transmits the targeted advertising 308 to the handheld glucose monitor 102 via the network 106. In one embodiment, the targeted advertising 308 is stored in the memory 204. The targeted advertising 308 may be output to the user 108 using any suitable output device, such as a display or a speaker, embodied within or coupled to the handheld glucose monitor 102.

In one embodiment, advertisers and/or marketers may configure one or more parameters associated with the advertising supply module 306. For example, the advertising supply module 306 may include parameters specifying which content in the advertising profile 302 and the diagnostic profile 304 that would trigger the advertising supply module 306 to transmit the targeted advertising 308 to the user 108 via the handheld glucose monitor 102. In one embodiment, the user may also configure one or more of the parameters. For example, the user may configure parameters to refuse advertising.

In one embodiment, the targeted advertising 308 is automatically provided to the user 108 via the handheld glucose monitor 102 without intervention from the user 108. Examples of the targeted advertising 308 include, but are not limited to, condition-related medical products, condition-related clothing, condition-related foods, and miscellaneous personal care items. For a diabetic, for example, the condition-related medical products may include glucose test strips and insulin, and the condition-related foods may include sugar-free and low-carbohydrate foods.

By automatically providing the targeted advertising 308 to the user 108, the handheld glucose monitor 102 may be financially supported by those advertisers and/or marketers providing the targeted advertising 308. For example, the advertisings and/or marketers may pay advertising fees for the advertising supply module 306 to transmit the targeted advertising 308 to the handheld glucose monitor 102. Those advertising fees may be used to subsidize the cost of the handheld glucose monitor 102.

FIG. 4 is a flow diagram illustrating a method 400 for receiving targeted advertising 308 at the handheld glucose monitor, in accordance with exemplary embodiments. According to the method 400, the advertising module 112 transmits (at 402) the advertising profile 302 and the diagnostic profile 304 to the advertising supply module 306. The advertising profile 302 may include any suitable advertising-related information about the user 108, such as the user's age, location, and health condition. The diagnostic profile 304 may include any suitable diagnostic data related to the user 108, such as the user's current and archived blood glucose levels, gathered by the handheld glucose monitor 102, according to one embodiment. The transmission of the advertising profile 302 and the diagnostic profile 304 may be initiated by the user 108 or automatically transmitted at given times or in response to given actions of the user 108.

According to exemplary embodiments, the advertising supply module 306 determines the targeted advertising 308 to transmit to the handheld glucose monitor 102 based on the advertising profile 302 and the diagnostic profile 304. In one example, the targeted advertising 308 may include businesses at or near the location of the user 108 provided in the advertising profile 302. In another example, the targeted advertising 308 may include medical products related to the diagnostic information provided in the diagnostic profile 304. The advertising module 112 receives (at 404) the targeted advertising 308 from the advertising supply module 306. The advertising module 112 outputs (at 406) the targeted advertising 308 to the user 108 via any suitable output device, such as a display or a speaker, embodied within or coupled to the handheld glucose monitor 102.

FIG. 5 is a block diagram illustrating an exemplary embodiment of a claims tracking system 500 including the handheld glucose monitor 102. The handheld glucose monitor 102 includes the claims tracking module 114 described in FIGS. 1 and 2. As illustrated in FIG. 5, the claims tracking module 114 includes a claims tracking profile 502 and the diagnostic profile 304. The claims tracking system 500 includes a cost data supply module 504. The handheld glucose monitor 102 is coupled to the cost data supply module 504 via the network 106. In one embodiment, the cost data supply module 504 is embodied within the glucose monitoring unit 104. In further embodiments, the cost data supply module 504 is separate from the glucose monitoring unit 104.

The claims tracking profile 502 may include any suitable claims tracking information about the user 108, such as the cost of office visits, the cost of medications, and other health-related costs. The health-related costs may be based on a current fee schedule or historic data based on what the user 108 paid in the past. The health-related costs may further be based on insurance-related costs, such as premiums, deductibles, and other out-of-pocket expenses. In one embodiment, the claims tracking profile 502 may include information regarding the insurance coverage (e.g., the name of the provider and the type of coverage) of the user 108. As previously described, the diagnostic profile 304 may include any suitable diagnostic data related to the user 108, such as the user's current and archived blood glucose levels, gathered by the handheld glucose monitor 102, according to one embodiment.

In one embodiment, the claims tracking module 114 transmits the claims tracking profile 502 and the diagnostic profile 304 to the cost data supply module 504 over the network 106. In response to receiving the claims tracking profile 502 and the diagnostic profile 304, the cost data supply module 504 determines the cost data 506 related to the user 108 based on the claims tracking profile 502 and the diagnostic profile 304 of the user 108. In one example, an improvement in the blood glucose level of the user 108 as shown in the diagnostic profile 304 may yield a decrease in the amount of drugs utilized by the user 108. Thus, depending on the information provided in the claims tracking profile 502, the decrease in the amount of drugs utilized by the user 108 may also yield a cost savings to the user 108. In another example, a worsening in the blood glucose level of the user 108 as shown in the diagnostic profile 304 may yield an increase in the amount of drugs utilized by the user 108. Thus, depending on the information provided in the claims tracking profile 502, the increase in the amount of drugs utilized by the user 108 may yield a cost increase to the user 108. According to exemplary embodiments, the cost savings and increase determined based on the claims tracking profile 502 and the diagnostic profile 304 are reflected in the cost data 506.

In one embodiment, the cost data supply module 504 transmits the cost data 506 to the handheld glucose monitor 102 via the network 106. In one embodiment, the cost data 506 is stored in the memory 204. The memory 204 may store the cost data 506 for any suitable time period. The cost data 506 may be output to the user 108 using any suitable output device, such as a display or a speaker, embodied within or coupled to the handheld glucose monitor 102. The cost data 506 output to the user 108 may include current cost data as well as historic cost data. By concurrently displaying the cost data 506 over an extended time period, the user 108 can easily view and compare fluctuations in health-related costs over the time period. The cost data 506 may be displayed in any suitable multimedia format, including, but not limited to, video, pictures, graphics, sound, and text.

The cost data 506 may include direct cost savings/increases and indirect cost savings/increases. Exemplary direct cost savings/increases may include, but are not limited to, a reduction or increase of emergency room ("ER") visits, a reduction or increase in medical supplies, and a reduction or increase in treatment and medication costs. Exemplary indirect cost savings/increases may include, but are not limited to, reduction or increase in missed time at work and a reduction or increase in disability costs. In one embodiment, the cost data 506 is determined based on a single user, such as the user 108. In further embodiments, the cost data 506 is aggregated based on a plurality of users. The cost data 506 may be output along with national averages of data related to the cost data 506 to provide a comparison between the cost data 506 and the national averages.

Figure 6:
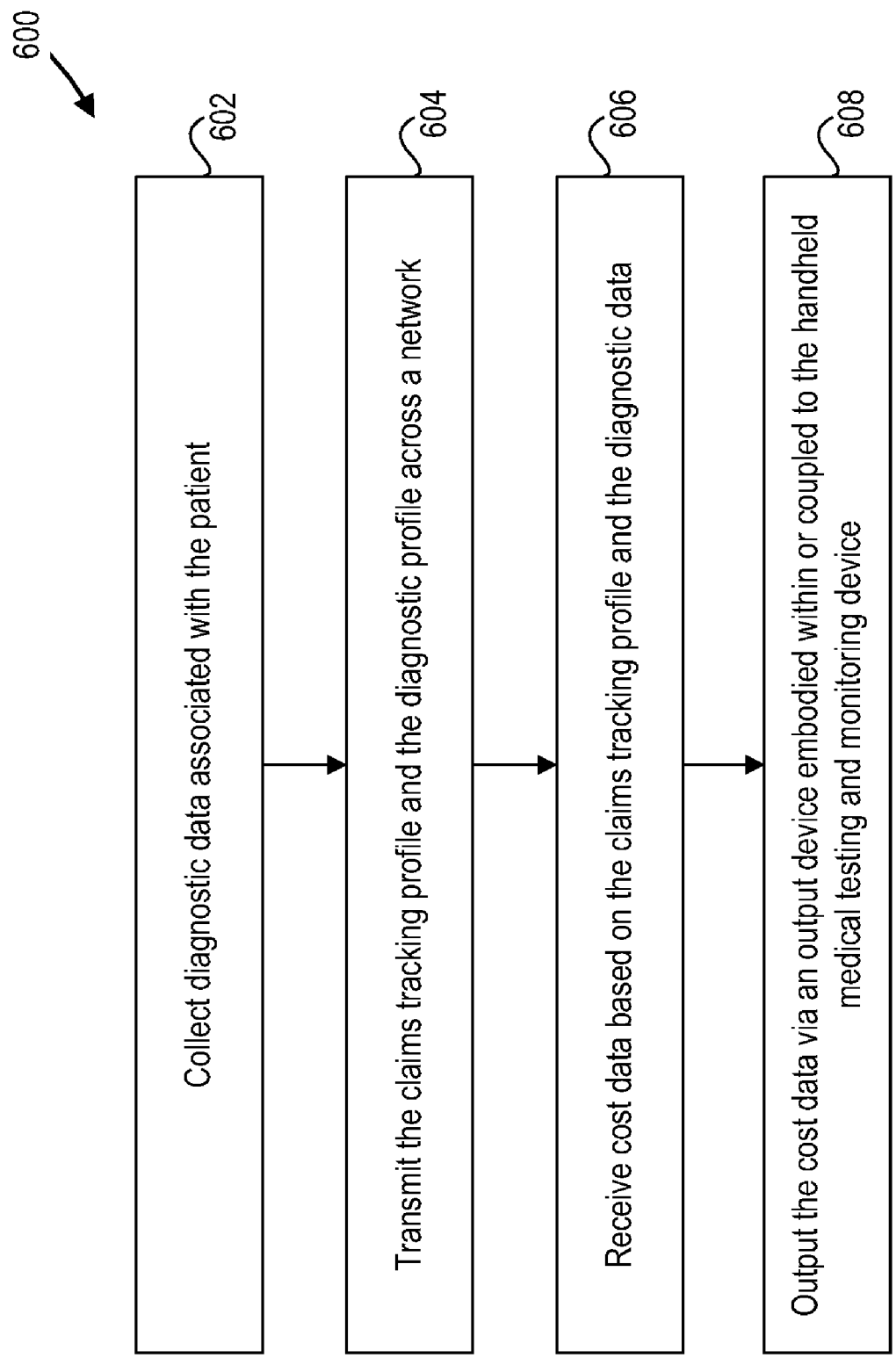
FIG. 6 is a flow diagram illustrating a method for generating cost data related to a diagnostic profile of a user, in accordance with exemplary embodiments.

FIG. 6 is a flow diagram illustrating a method 600 for generating cost data, such as the cost data 506, related to the diagnostic profile 304 of the user 108, in accordance with exemplary embodiments. A handheld medical testing and monitoring device, such as the handheld glucose monitor 102, collects (at 602) diagnostic data related to the user 108. In one embodiment, the collected diagnostic data is stored within the diagnostic profile 304. The handheld glucose monitor 102 may collect, for example, the current blood glucose level of the user 108. In one embodiment, the user 108 utilizes a lancing device (not shown) on the handheld glucose monitor 102 to draw blood for blood glucose testing. The claims tracking module 114 transmits (at 604) via the network 106 the claims tracking profile 502 and the diagnostic profile 304 to the cost data supply module 504.

In response to receiving the claims tracking profile 502 and the diagnostic profile 304, the cost data supply module 504 determines the cost data 506 related to the user 108 based on the claims tracking profile 502 and the diagnostic profile 304 of the user 108. The diagnostic profile 304 may indicate the health condition of the user. The claims tracking profile 502 may provide claims tracking information (e.g., the cost of office visits, the cost of medications, and other health-related costs). The cost data 506 may indicate, for example, a cost savings or a cost increase, based on the claims tracking profile 502 and the diagnostic profile 304. The claims tracking module 114 receives (at 606) the cost data 506 from the cost data supply module 504. The claims tracking module 114 outputs (at 608) the cost data 506 to the user 108 using any suitable output device, such as a display or a speaker, embodied within or coupled to the handheld glucose monitor 102.

Figure 7:
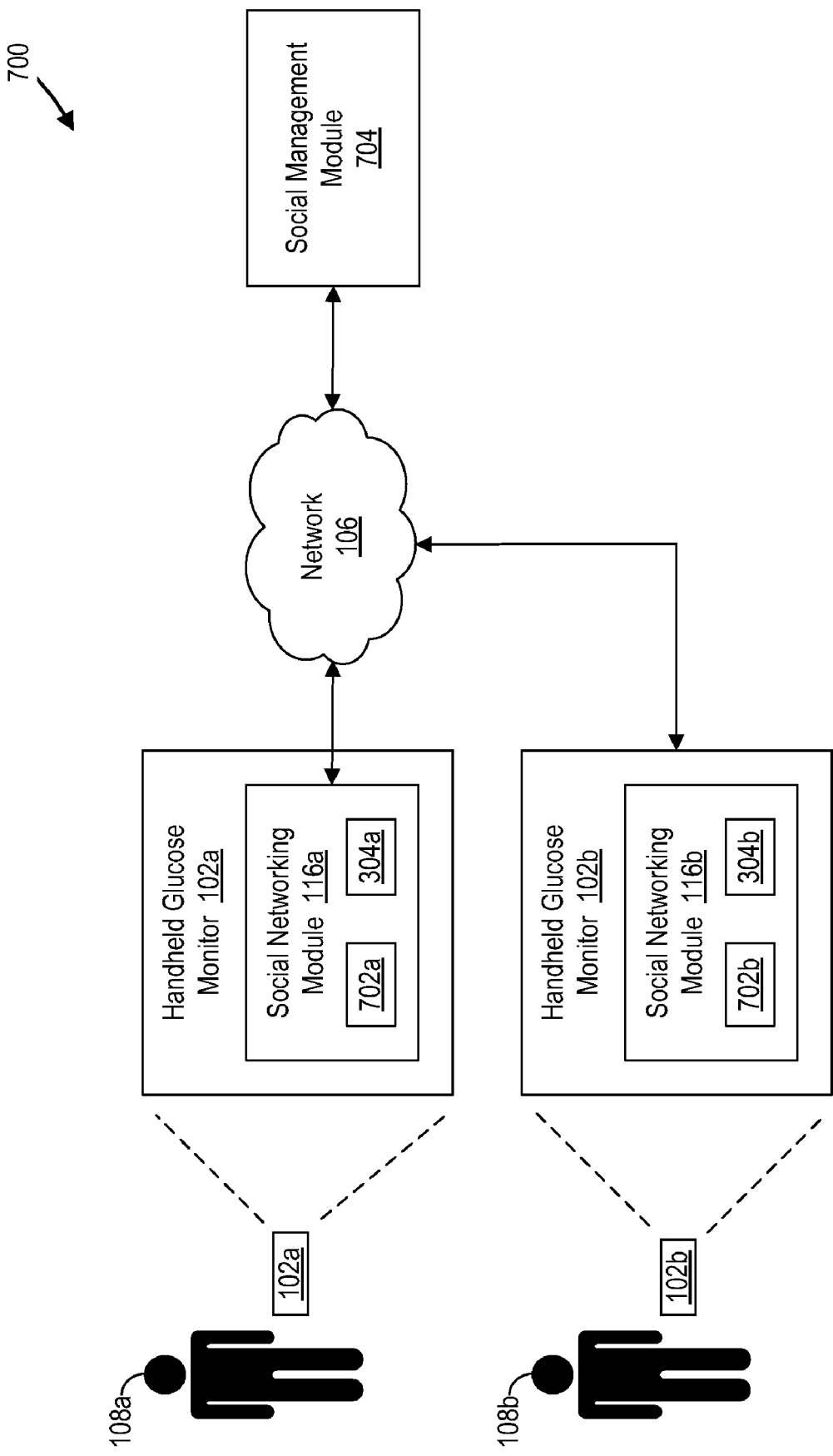
FIG. 7 is a block diagram illustrating a social networking system including a first handheld glucose monitor and a second handheld glucose monitor, in accordance with exemplary embodiments.

FIG. 7 is a block diagram illustrating an exemplary embodiment of a social networking system 700 including a first handheld glucose monitor 102a and a second handheld glucose monitor 102b. As illustrated in FIG. 7, the first handheld glucose monitor 102a includes a first social networking module 116a, and the second handheld glucose monitor 102b includes a second social networking module 116b. The social networking system 700 further includes a social management module 704. The handheld glucose monitors 102a and 102b are coupled to the social management module 704 via the network 106. In one embodiment, the social management module 704 is embodied within the glucose monitoring unit 104. In further embodiments, the social management module 704 is separate from the glucose monitoring unit 104.

According to exemplary embodiments, the first social networking module 116a includes the first social networking profile 702a and a first diagnostic profile 304a. The first social networking profile 702a and the first diagnostic profile 304a are associated with a first user 108a. The second social networking module 116b includes the second social networking profile 702b and a second diagnostic profile 304b. The second social networking profile 702b and the second diagnostic profile 304b are associated with a second user 108b. The social networking profiles 702a and 702b may include medical information, such as insulin dosages of the users 108a and 108b, respectively, and non-medical information, such as hobbies of the users 108a and 108b, respectively. In one embodiment, the social networking profiles 702a and 702b may include similar information provided in the advertising profile 302 and the claims tracking profile 502, such as the users' ages, locations, health conditions, and health care costs. The first diagnostic profile 304a includes diagnostic data about the first user 108a collected by the first handheld glucose monitor 102a. The second diagnostic profile 304b includes diagnostic data about the second user 108b collected by the second handheld glucose monitor 102b. An example of diagnostic data collected by the handheld glucose monitors 102a and 102b includes the current blood glucose levels of the users 108a and 108b, respectively.

According to exemplary embodiments, the social management module 704 coordinates communications between a plurality of users, such as the users 108a and 108b, over the network 106. For example, the social management module 704 may coordinate communications between the first user 108a and the second user 108b via the first handheld glucose monitor 102a and the second handheld glucose monitor 102b, respectively. Exemplary communications may include, but are not limited to, text messages, electronic mail ("email"), photos, audio messages, and video messages. By incorporating a social networking component into the handheld glucose monitors 102a and 102b, the users 108a and 108b may enjoy a richer experience than simply testing their blood glucose levels.

In one embodiment, the first user 108a is identified by a first buddy name or other unique identifier ("ID"), and the second user 108b is identified by a second buddy name or other unique ID. The use of buddy names may enable the users 108a and 108b to communicate with each other anonymously. For example, if the first user 108a desires to send a communication to the second user 108b, the social networking system 700 may be configured such that the first user 108a sends the communication to the second user 108b using only the second buddy name. That is, the second buddy name may hide personal information of the second user 108b, such as the user's name, address, and phone number.

In one embodiment, when a user, such as the first user 108a, desires to participate in the social networking system 700, the first user 108a registers with the social management module 704. In one embodiment, the process for registering the first user 108a includes choosing a buddy name and transmitting the first social networking profile 702a and the first diagnostic profile 304a to the social management module 704. In further embodiments, the first user 108a may establish a new profile with the social management module 704 during the registration process or decide to send one or the other of the first social networking profile 702a and the first diagnostic profile 304a. In one embodiment, the social management module 704 searches for one or more other users on the network 106 based on the first social networking profile 702a. The social management module 704 may search under any suitable criteria including, but not limited to, a similar medical condition, a similar location, and/or similar hobbies. In one embodiment, the social management module 704 searches the other users dynamically. For example, the social management module 704 may dynamically retrieve the second social networking profile 702b and the second diagnostic profile 304b from the second handheld glucose monitor 102b to compare with the first social networking profile 702a and the first diagnostic profile 304a. In further embodiments, the social management module 704 searches a database containing data of the other users. For example, the database may be previously populated with the second social networking profile 702b and the second diagnostic profile 304b, so that a comparison may be made with the first social networking profile 702a and the first diagnostic profile 304a without dynamically retrieving the second social networking profile 702b and the second diagnostic profile 304b.

When the social management module 704 finds one or more users, such as the second user 108b, with similar criteria to the first user 108a, the social management module 704 populates a buddy list associated with the first user 108a with the buddy name of the second user 108b. To facilitate a more active social network, the social management module 704 may automatically populate the buddy list associated with the first user 108a with at least one user, such as the second user 108b.

If, for example, the second user 108b matches the first user 108a under the criteria utilized by the social management module 704, then the social management module 704 may populate buddy lists on the first handheld glucose monitor 102a and the second handheld glucose monitor 102b. The buddy lists may be accessible through input and output interfaces, such as a stylus and a display, on the handheld glucose monitors 102a and 102b. In one embodiment, each buddy name on the buddy list is associated with a buddy profile, which is associated with a user, such as the users 108a and 108b. For example, the first user 108a may desire to share her location, medical condition, and the first diagnostic profile 304a. If the first user 108a is on the buddy list of the second user 108b, then the second user 108b may be able to view the buddy profile of the first user 108a. In particular, the second user 108b may be able to view the progress of the first user 108a by accessing the first diagnostic profile 304a. If the first diagnostic profile 304a indicates that the health condition of the first user 108a has improved, then the second user 108b may send a communication of congratulations to the first user 108a. If, on the other hand, the first diagnostic profile 304a indicates that the health condition of the first user 108a has not improved or worsened, then the second user 108b may send a communication of encouragement to the first user 108a. The communications sent between users, such as the users 108a and 108b, may be manually entered or selected from a plurality of pre-defined communications. By enabling the sharing of the diagnostic profile 304 between users, such as the users 108a and 108b, the social management module 704 may create a collaborative wellness network promoting behavioral modification.

FIG. 8 is a flow diagram illustrating a method 800 for providing social interaction between the first handheld glucose monitor 102a and the second handheld glucose monitor 102b, in accordance with exemplary embodiments. According to the method 800, the social management module 704 receives (at 802) the first social networking profile 702a and the first diagnostic profile 304a from the first handheld glucose monitor 102a. The social management module 704 selects (at 804) the second user 108b, who is associated with the second social networking profile 702b and the second diagnostic profile 304b. In one embodiment, the second user 108b may be selected because of similarities between the first social networking profile 702a and the second social networking profile 702b, as well as similarities between the first diagnostic profile 304a and the second diagnostic profile 304b.

In one embodiment, the social management module 704 dynamically retrieves the second social networking profile 702b and the second diagnostic profile 304b from the second handheld glucose monitor 102b to compare with the first social networking profile 702a and the first diagnostic profile 304a. In further embodiments, the first social networking profile 702a and the first diagnostic profile 304a are compared with a database that is previously populated with the second social networking profile 702b and the second diagnostic profile 304b.

The social management module 704 determines (at 806) whether second user 108b has allowed the sharing of the second social networking profile 702b and/or the second diagnostic profile 304b. In one embodiment, the second user 108b may decide which portions, if any, of the second social networking profile 702b and the second diagnostic profile 304b to share. For example, the second user 108b may not want to share certain personal data.

If the second user 108b has allowed sharing, the social management module 704 populates (at 808) a user list (e.g., a buddy list) at the first handheld glucose monitor 102a with a unique identifier (e.g., buddy name), the second social networking profile 702b, and the second diagnostic profile 304b associated with the second user 108b. If the second user 108b has not allowed sharing, the social management module 704 populates (at 810) the user list at the first handheld glucose monitor 102a with the unique identifier associated with the second user 108b, but without the second social networking profile 702b and the second diagnostic profile 304b. The unique identifier may enable the first user 108a to communicate with the second user 108b via the first handheld glucose monitor 102a. In further embodiments, in response to populating the user list at the first handheld glucose monitor 102a of the first user 108a, the social management module 704 populates a user list at the second handheld glucose monitor 102b of the second user 108b. For example, the user list at the second handheld glucose monitor 102b may be populated with a unique identifier associated with the first user 108a, the first social networking profile 702a, and/or the first diagnostic profile 304a associated with the first user 108a may be populated in a user list at the second handheld glucose monitor 102b depending on whether the first user 108a has allowed or not allowed sharing.

Although the subject matter presented herein has been described in conjunction with one or more particular embodiments and implementations, it is to be understood that the embodiments defined in the appended claims are not necessarily limited to the specific structure, configuration, or functionality described herein. Rather, the specific structure, configuration, and functionality are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the embodiments, which is set forth in the following claims.

What is claimed is:

1. A method for providing social interaction between a first handheld and portable medical testing and monitoring device and a second handheld and portable medical testing and monitoring device, comprising:
  receiving a social networking profile from the first handheld and portable medical testing and monitoring device associated with a first patient, the first handheld and portable medical testing and monitoring device configured to acquire first diagnostic data regarding the first patient and transmit the first diagnostic data over a network to a first healthcare provider;
  generating, through the first handheld and portable medical testing and monitoring device, a diagnostic profile of the first patient, the diagnostic profile containing current and archived diagnostic information of the first patient including the first diagnostic data, the diagnostic profile stored on the first handheld and portable medical testing and monitoring device;
  receiving the diagnostic profile from the first handheld and portable medical testing and monitoring device;
  selecting a second patient associated with the second handheld and portable medical testing and monitoring device based on the social networking profile and the diagnostic profile indicating compatibility between the first patient and the second patient, the second handheld and portable medical testing and monitoring device configured to acquire second diagnostic data regarding the second patient and transmit the second diagnostic data over the network to a second health-care provider; and
  populating a user list at the second handheld and portable medical testing and monitoring device with a unique identifier of the first patient enabling the second patient to communicate with the first patient, via the unique identifier, by way of the second handheld and portable medical testing and monitoring device.

2. The method of claim 1, wherein the social networking profile comprises a health condition of the first patient.

3. The method of claim 2, wherein the social networking profile further comprises an age and a location of the first patient.

4. The method of claim 1, wherein the diagnostic information comprises current and archived blood glucose levels of the first patient acquired via the first handheld and portable medical testing and monitoring device.

5. The method of claim 1, further comprising:
  in response to populating the user list at the first handheld and portable medical testing and monitoring device with the unique identifier, transmitting the diagnostic profile from the first handheld and portable medical testing and monitoring device to the second handheld and portable medical testing and monitoring device via the unique identifier.

6. The method of claim 1, further comprising:
  receiving a selection of the unique identifier in a graphical user interface displayed on the second handheld and portable medical testing and monitoring device;
  in response to receiving the selection of the unique identifier, displaying in the graphical user interface a plurality of communications related to changes to the diagnostic profile associated with the unique identifier, the plurality of communications including communications of encouragement and communications of congratulations;
  receiving, through the graphical user interface, a selection of at least one of the plurality of communications; and
  in response to receiving, through the graphical user interface, the selection of the at least one of the plurality of communications, transmitting the at least one of the plurality of communications from the second handheld and portable medical testing and monitoring device to the first handheld and portable medical testing and monitoring device.

7. The method of claim 1, further comprising:
  displaying the user list on the second handheld and portable medical testing and monitoring device; and
  initiating, at a request of the second patient via the unique identifier, communications between the first patient and the second patient via the first handheld and portable medical testing and monitoring device and the second handheld and portable medical testing and monitoring device.

8. A system for providing social interaction between a first handheld and portable medical testing and monitoring device and a second handheld and portable medical testing and monitoring device, comprising:
  a memory for storing a program containing code for providing social interaction between the first handheld and portable medical testing and monitoring device and the second handheld and portable medical testing and monitoring device;
  a processor functionally coupled to the memory, the processor being responsive to computer-executable instructions contained in the program and operative to at least:
    receive a social networking profile from the first handheld and portable medical testing and monitoring device associated with a first patient, the first handheld and portable medical testing and monitoring device configured to acquire first diagnostic data regarding the first patient and transmit the first diagnostic data over a network to a first healthcare provider,
    generate, through the first handheld and portable medical testing and monitoring device, a diagnostic profile of the first patient, the diagnostic profile containing current and archived diagnostic information of the first patient including the first diagnostic data, the diagnostic profile stored on the first handheld and portable medical testing and monitoring device, receive the diagnostic profile from the first handheld and portable medical testing and monitoring device, select a second patient associated with the second handheld and portable medical testing and monitoring device based on the at least one of the social networking profile and the diagnostic profile indicating compatibility between the first patient and the second patient, the second handheld and portable medical testing and monitoring device configured to acquire second diagnostic data regarding the second patient and transmit the second diagnostic data over the network to a second health-care provider, and populate a user list at the second handheld and portable medical testing and monitoring device with a unique identifier of the first patient enabling the second patient to communicate with the first patient, via the unique identifier, by way of the second handheld and portable medical testing and monitoring device.

9. The system of claim 8, wherein the social networking profile comprises a health condition of the first patient.

10. The system of claim 8, wherein the diagnostic information comprises current and archived blood glucose levels of the first patient acquired via the first handheld and portable medical testing and monitoring device.

11. The system of claim 8, wherein the processor is further operative to at least:

in response to populating the user list at the first handheld and portable medical testing and monitoring device with the unique identifier, transmit the diagnostic profile from the first handheld and portable medical testing and monitoring device to the second handheld and portable medical testing and monitoring device via the unique identifier.

12. The system of claim 8, wherein the processor is further operative to at least:

receive a selection of the unique identifier in a graphical user interface displayed on the first handheld and portable medical testing and monitoring device, in response to receiving the selection of the unique identifier, display in the graphical user interface a plurality of communications related to changes to the diagnostic profile, the plurality of communications including communications of encouragement and communications of congratulations, receive, through the graphical user interface, a selection of at least one of the plurality of communications; and in response to receiving, through the graphical user interface, the selection of the at least one of the plurality of communications, transmit the at least one of the plurality of communications from the second handheld and portable medical testing and monitoring device to the first handheld and portable medical testing and monitoring device.

13. The system of claim 8, wherein the processor is further operative to at least:

display the user list on the second handheld and portable medical testing and monitoring device; and initiate, at a request of the second patient via the unique identifier, communications between the first patient and the second patient via the first handheld and portable medical testing and monitoring device and the second handheld and portable medical testing and monitoring device.

14. A computer-readable medium having instructions stored thereon for execution by a processor to perform a method for providing social interaction between a first handheld and portable medical testing and monitoring device and a second handheld and portable medical testing and monitoring device, the method comprising:

receiving a social networking profile from the first handheld and portable medical testing and monitoring device associated with a first patient, the first handheld and portable medical testing and monitoring device configured to acquire first diagnostic data regarding the first patient and transmit the first diagnostic data over a network to a first healthcare provider;

generating, through the first handheld and portable medical testing and monitoring device, a diagnostic profile of first patient, the diagnostic profile containing current and archived diagnostic information of the first patient including the first diagnostic data, the diagnostic profile stored on the first handheld and portable medical testing and monitoring device;

receiving the diagnostic profile from the first handheld and portable medical testing and monitoring device;

selecting a second patient associated with the second handheld and portable medical testing and monitoring device based on the at least one of the social networking profile and the diagnostic profile indicating compatibility between the first patient and the second patient, the second handheld and portable medical testing and monitoring device configured to acquire second diagnostic data regarding the second patient and transmit the second diagnostic data over the network to a second healthcare provider; and populating a user list at the second handheld and portable medical testing and monitoring device with a unique identifier of the first patient enabling the second patient to communicate with the first patient, via the unique identifier, by way of the second handheld and portable medical testing and monitoring device.

15. The computer-readable medium of claim 14, wherein the social networking profile comprises a health condition of the first patient.

16. The computer-readable medium of claim 15, wherein the social networking profile further comprises an age and a location of the first patient.

17. The computer-readable medium of claim 14, wherein the diagnostic information comprises current and archived blood glucose levels of the first patient acquired via the first handheld and portable medical testing and monitoring device.

18. The computer-readable medium of claim 14, the method further comprising:

in response to populating the user list at the first handheld and portable medical testing and monitoring device with the unique identifier, transmitting the diagnostic profile from the first handheld and portable medical testing and monitoring device to the second handheld and portable medical testing and monitoring device via the unique identifier.

19. The computer-readable medium of claim 14, the method further comprising:

receiving a selection of the unique identifier in a graphical user interface displayed on the first handheld and portable medical testing and monitoring device;

in response to receiving the selection of the unique identifier, displaying in the graphical user interface a plurality of communications related to changes to the diagnostic profile, the plurality of communications including communications of encouragement and communications of congratulations; and receiving, through the graphical user interface, a selection of at least one of the plurality of communications; and in response to receiving, through the graphical user interface, the selection of the at least one of the plurality of communications, transmitting the at least one of the plurality of communications from the second handheld and portable medical testing and monitoring device to the first handheld and portable medical testing and monitoring device.

20. The computer-readable medium of claim 14, the method further comprising:

displaying the user list on the second handheld and portable medical testing and monitoring device; and initiating, at a request of the second patient via the unique identifier, communications between the first patient and the second patient via the first handheld and portable medical testing and monitoring device and the second handheld and portable medical testing and monitoring device.

* * * * *